(12) United States Patent
Lackey et al.

(10) Patent No.: US 6,506,152 B1
(45) Date of Patent: Jan. 14, 2003

(54) CALORIC ENERGY BALANCE MONITOR

(76) Inventors: Robert P. Lackey, 3338 Fosca St., Carlsbad, CA (US) 92009; Darrel D. Drinan, 10914 Caminito Tierra, San Diego, CA (US) 92131; Michael W. MacCollum, 14188 Woodcreek Rd., Poway, CA (US) 92064; Tanya L. Liesz, 2469 Manchester, Cardiff, CA (US) 92007; Fred B. Schlador, 1425 Cressa Ct., Carlsbad, CA (US) 92009; Diethard A. Merz, 3667 32nd St., San Diego, CA (US) 92104

( * ) Notice: Subject to any disclaimer, the term of this patent is extended or adjusted under 35 U.S.C. 154(b) by 0 days.

(21) Appl. No.: 09/567,799

(22) Filed: May 9, 2000

(51) Int. Cl.[7] .................................................. A61B 5/00
(52) U.S. Cl. ....................................... 600/300; 128/921
(58) Field of Search ................................ 600/300, 547, 600/301; 128/920–925; 434/127; 706/15, 16, 21

(56) References Cited

U.S. PATENT DOCUMENTS

| | | | |
|---|---|---|---|
| 5,749,372 A | | 5/1998 | Allen et al. |
| 5,817,031 A | * | 10/1998 | Masuo et al. ................ 600/547 |
| 5,989,188 A | * | 11/1999 | Birkhoelzer et al. ......... 600/300 |
| 6,095,949 A | * | 8/2000 | Arai ............................ 434/127 |

OTHER PUBLICATIONS

Daniel S. Jafer, M.D. Beeper–sized Exercise Monitors Help People Lose Weight, Study Says; San Francisco Chronicle Associated Press Byline, Jun. 5, 1998.

Gregory S. Ellis, PH.D. Dr.Ellis's Fitness Guide The Caltrac 100/100 Plan book of The Caltrac System to Help You Control Your Weight and Improve your Health; Muscle Dynamics Fitness Network, 1993, Torrance CA.

Caltrac Instruction Manual; Muscle Dynamics Fitness Network, 1993; DSA Member Direct Selling Association.

BioTrainer Instruction Manual; Web site: www.imsystems.net; Published by IM Systems Baltimore MD.

Kathy Smith's Peak Fat Burning; Stuff We Love–Trade in your Trainer–For A Biotrainer; Weight Loss Magazine, p. 8, Date Unknown.

The American Journal of Clinical Nutrition Official Journal of the American Society for Clinical Nutrition, Inc; Sep. 1996, vol. 64, No. 3(S), IssN 0002–9165, "Why Bioelectrical Impedance Analysis Should Be Used For Estimating Adiposity", p. 436s–448s.

Paul J. Arciero, Michael I. Goran, and Eric T. Poehlman; Resting MetabolicRate Is Lower In Women Than In Men; The American Physiological Society 1993, p. 2514–2520.

* cited by examiner

*Primary Examiner*—Eric F. Winakur
*Assistant Examiner*—David McCrosky
(74) *Attorney, Agent, or Firm*—Morgan, Lewis & Bockius, LLP

(57) ABSTRACT

A caloric energy balance monitor uses calories expended during rest and activity, and calories consumed from food, to compute a predicted change in the user's body fat percentage. The predicted change in body fat percentage is then compared to an actual change in body fat percentage to iteratively compute a correction factor that is used in subsequent measurements of net caloric energy balance.

11 Claims, 3 Drawing Sheets

CALORIC ENERGY BALANCE MONITOR

RELATED APPLICATIONS

This application refers to, and incorporates by reference the disclosure of, application Ser. No. 09/291,546, filed on Apr. 14, 1999.

BACKGROUND OF THE INVENTION

1. Field of the Invention

The present invention relates generally to the measurement of metabolism activity, and more particularly, to the measurement of an individual's caloric energy balance.

2. Description of the Related Art

Many individuals are concerned with their body weight for reasons of health and personal appearance. Despite constant warnings by the media that excessive body weight and high body fat percentages are associated with such negative health factors as hypertension, heart disease and diabetes, and is thus detrimental to an individual's well-being and life expectancy, an overall decrease in physical activity has resulted in an increasing number of overweight and often seriously obese individuals.

It is generally known that an individual's body fat is related to caloric energy balance, which is the difference between caloric intake (calories consumed from food), and caloric expenditure (calories that are burned by base metabolism and physical activity). If an individual expends more calories than are consumed, he or she will lose fat. Conversely, if an individual expends fewer calories than consumed, he or she will gain fat. For a typical individual, a net positive or negative balance of 3,500 calories will cause, respectively, a gain or a loss of one pound of fat.

An effective way of controlling body fat is to monitor, on a regular basis, individual net caloric energy balance to establish an individual exercise regimen in which net caloric energy balance will be zero or negative. To aid in this process, various products have been developed and marketed that measure an individual's daily caloric expenditure from the user's rest or base metabolic rate and his or her level of physical activity. A product of this type is described in U.S. Pat. No. 5,749,372. Products have also been developed which allow an individual to keep track of daily or weekly caloric input.

Although presently-existing products theoretically provide a mechanism for predicting body fat percentage changes from caloric balance information, the accuracy of the prediction is quite poor. As a result, some individuals may lose weight, despite the fact that these prior art devices predict an increase in body fat percentages. Other individuals may be disappointed when these devices predict a decrease in body fat percentage, but no such change ever materializes. Major deficiencies in these products are their inabilities to, (1) account for changes in the user's base metabolic rate (which typically occur during an exercise course that may include aerobic activity and weight training), (2) accurately monitor physical activity and (3) allow the convenient and accurate entry of caloric consumption information. As a result, presently existing caloric monitoring products produce erroneous indications of the individual's base metabolic rate, activity calories expended and calories consumed, which in turn, produce erroneous measurements of caloric energy balance.

Thus, there is a need for an improved, more accurate device for measuring and monitoring an individual's net caloric energy balance. There is also a need for a monitoring device, which considers variations in an individual's body fat percentage over time.

SUMMARY OF THE INVENTION

A novel caloric energy balance monitor predicts changes in an individual's body fat or body fat percentage based upon the individual's caloric balance. Caloric balance is determined from an individual's base metabolic rate, physical activity, and caloric consumption. To achieve increased prediction accuracy over time, the monitor calculates a correction factor by comparing predicted and actual changes in the individual's body fat or body fat percentage. The monitor utilizes this correction factor in subsequent computations of caloric balance so as to more accurately predict subsequent changes in body fat or body fat percentage.

An individual's base metabolic rate (BMR, in units of calories) is averaged over a period of time and then added to the calories expended during physical activity. BMR is indicative of calories that are burned by an individual at rest. Calories burned as a result of exercise as well as BMR are then subtracted from averaged caloric consumption. Caloric consumption is determined by the caloric content of foods consumed over a given time period. The result of this calculation provides an indication of a net caloric energy increase or decrease. This indication may then be integrated and averaged to compute a predicted change in body fat or body fat percentage.

The user's current body fat percentage is compared to a known previous body fat percentage for the user so as to obtain the actual change in body fat percentage. That difference is used to calculate a correction factor, which is preferably integrated over a 24-hour period, converted to calories, and combined with the caloric input at the summer in subsequent computations of the predicted change in body fat percentage.

Thus, for example, if the predicted body fat percentage change over a period of one week were −1/2%, and there was no actual change in the individual's body fat percentage, then the correction factor would be 1/14% per day (1/2% error over 7 days). Since the conversion of "a pound" of body fat to calories is 3,500 calories, the correction factor would be 3,500/14 or +250 calories per day, spread or averaged over a 24-hour period. This correction factor is added to the of activity, rest and input calories to compute a subsequent value of predicted change in body fat percentage.

Pursuant to an illustrative embodiment of the invention disclosed herein, the individual's estimated at "base metabolic rate" (BMR) and current actual body fat percentage may be obtained from a body composition analyzer of the type disclosed in the above-referenced co-pending application. The base metabolic rate is a function of the individual's fat-free mass, which may be computed in the body composition analyzer, using of any of several known algorithms, one of which is described in an article entitled, "*Resting Metabolic Rate Is Lower In Women Than In Men*", published in 1993 in the *American Physioloical Society* 0161-7567/93 at page 2514.

BRIEF DESCRIPTION OF THE DRAWINGS

The present invention along with further objects and advantages thereof may best be understood by reference to the following description taken in conjunction with the accompanying drawings, in which.

DETAILED DESCRIPTION OF THE INVENTION

In broad overview, the caloric energy balance monitor of the invention combines measurements of base metabolic rate, including digestion, with calories expended in physical activity, and calories consumed by the intake of food. Since the ability to accurately measure or input each of these data is somewhat limited, the caloric energy monitor of the invention computes a correction factor (CF) in accordance with the following relationship:

(CALORIES CONSUMED)+*CF*−(CALORIES EXPENDED BY BASE METABOLIC RATE)−(CALORIES EXPENDED DURING ACTIVITY)=CALORIC BALANCE

The energy balance monitor of this invention may be used in conjunction with a body composition analyzer of the type disclosed in copending application Ser. No. 09/291,546. The body composition analyzer, as described in that application, computes certain body composition factors such as the user's body fat percentage, that is, the ratio of pounds of fat and total weight, and the user's fat-free mass.

It is not necessary to enter the caloric consumption values of the preceding formula into the caloric balance energy monitor. A "typical" or "estimated" value can be provided by the energy monitor itself, and/or by an ancillary body composition analyze. Errors in this estimate will be later corrected by use of the previously described correction factor.

Figure 1:
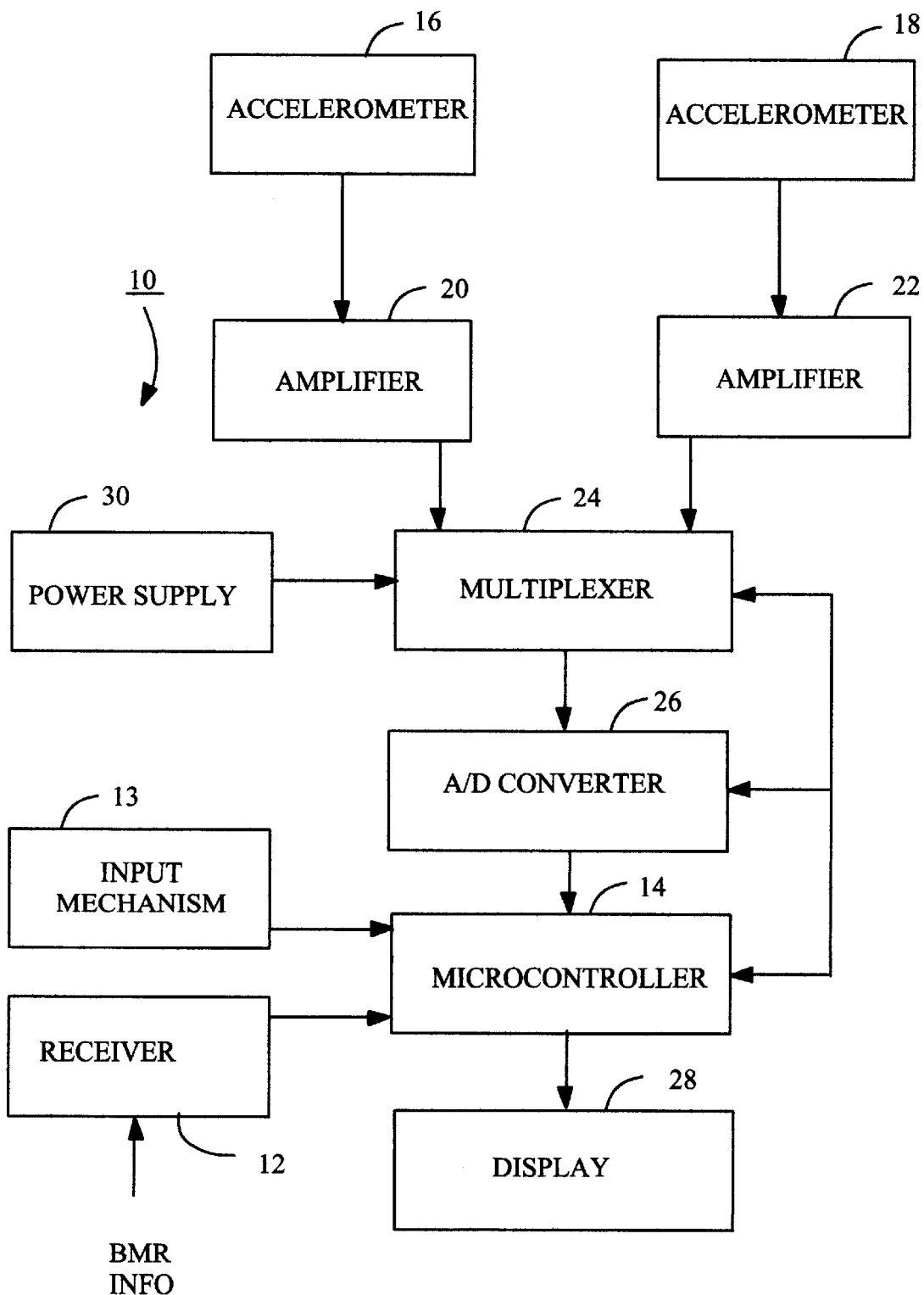
FIG. 1 is a block diagram of a caloric energy balance monitor in accordance with an embodiment of the present invention.

As shown in FIG. 1, the caloric energy balance monitor 10 includes a receiver 12, which receives information regarding the user's current body fat percentage and fat free mass, and the base metabolic rate, from the body composition analyzer (not shown) through a communications link. This communications link may be implemented using any technique for conveying information from one place to another, including wireless communication, wired communication, optical communication, and other types of links not specifically enumerated herein. For example, one illustrative communications link is implemented using modulated electromagnetic signals to transfer information between the body composition analyzer and the caloric balance monitor 10.

The user's caloric intake or consumption, based on the amount of food eaten by the user during a given interval (e.g. 24 hours), is determined from information input by the user to input mechanism 13. Input mechanism 13 represents any mechanism adapted to accept input data, illustrative examples of which are contact switches, keypads, a keyboard, a disk drive, an RF interface, a smart card reader, a magnetic strip reader, and other input devices not explicitly enumerated herein. Input mechanism 13 is adapted to permit a user to input his or her food consumption calories into monitor 10.

In the illustrative example of FIG. 1, input mechanism 13 is connected to one input of a microcontroller 14. A separate input of microcontroller 10 receives data from an output of receiver 12. The user's physical activity, such as during an exercise program, is measured by the use of a pair of accelerometers 16 and 18. These accelerometers may, but need not, be in the form of piezoelectric transducers that sense, in a manner disclosed in U.S. Pat. No. 5,749,372, the user's acceleration during physical activity such as walking, jogging, running on a treadmill, or performing aerobic exercise. When monitor 10 is worn on the user's waist or belt during such activity, the use of two accelerometers oriented perpendicularly to one another (see FIG. 4) increases accuracy of measurement by sensing the acceleration produced by body motion in three mutually orthogonal directions. When less accuracy is acceptable, only a single accelerometer may be used to monitor activity.

Continuing with the illustrative hardware configuration of FIG. 1, the outputs of accelerometers 16, 18 are respectively amplified in amplifiers 20 and 22, the outputs of which are applied to the inputs of a multiplexer 24. The output of multiplexer 24 is applied to the input of an analog-to-digital converter 26, and the output of the digital-to-analog converter 26 is applied to another input of microcontroller 14. Control signals derived in the microcontroller 14 are applied to multiplexer 24 and converter 26 to control their operation, and another output of microcontroller 14 is applied to a display 28 which is shown in greater detail in FIG. 3. Appropriate operating voltages for the components of the monitor 10 are provided by a power supply 30.

Figure 2:
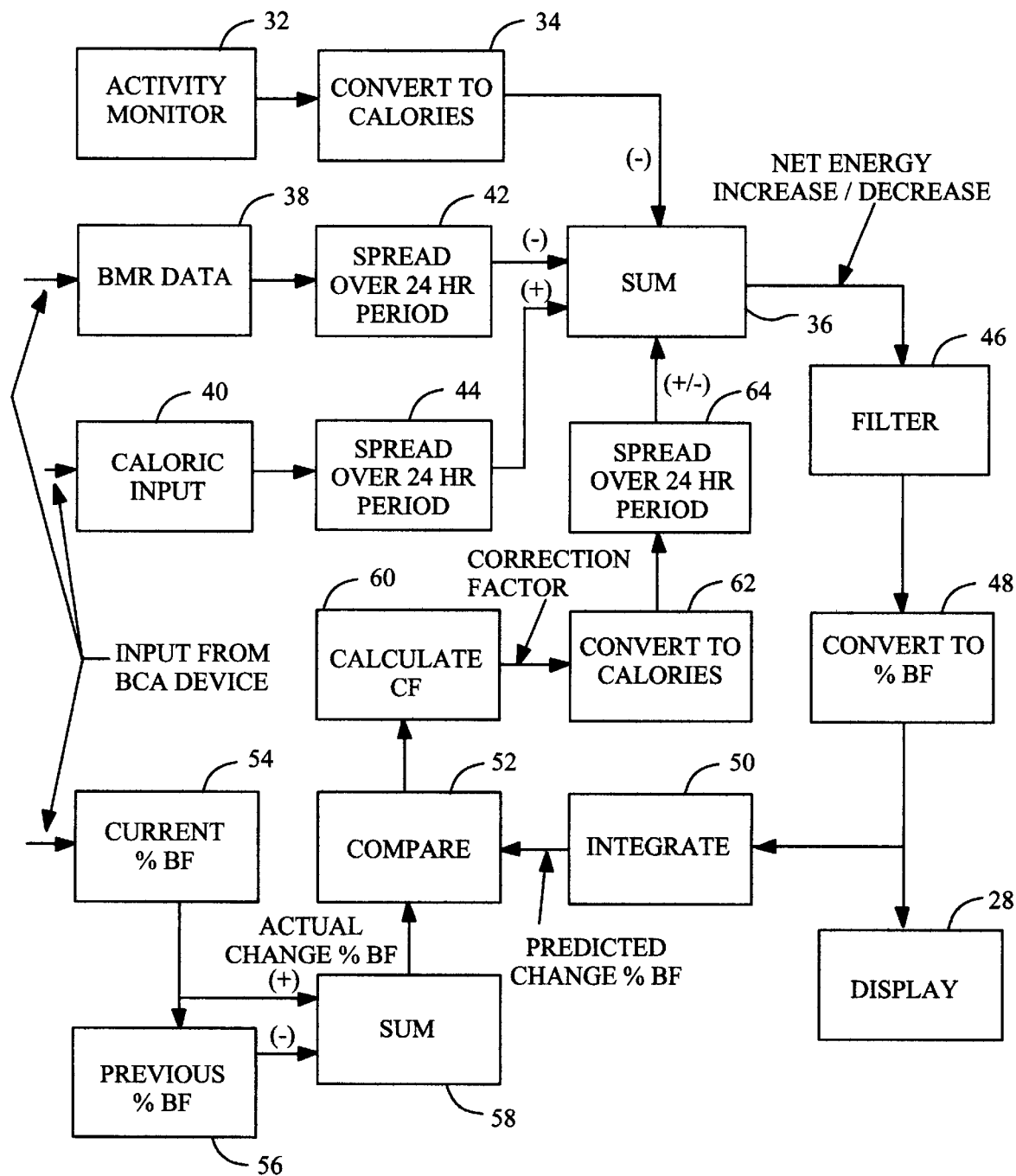
FIG. 2 is a function flow chart describing the operation of the caloric energy balance monitor of FIG. 1.

The operation of the caloric energy balance monitor 10 of FIG. 1 is described in the functional flow chart of FIG. 2. As shown therein, the information of the user's activity, as derived from the accelerators 16 and 18 and as indicated at activity monitor 32, is converted to calories at 34 and that caloric value is applied to a negative input of a summer 36.

The user's base metabolic rate (in calories) is input as indicated at 38, and the user's caloric input or consumption from food eaten during a given period, e.g. 24 hours, is applied at 40. In a preferred embodiment of the invention, the base metabolic rate and caloric input are derived separately from an external unit such as the body composition analyzer disclosed in the above-referenced copending patent application. Alternatively, the difference between these data in calories may be input directly to the monitor 10 since, as described below, these two terms are subtracted from each other in the monitor.

Whereas the user's activity may be monitored in real time, the BMR and caloric data input can be integrated over a 24-hour period and thus averaged at 42 and 44, respectively, and are thus spread over a selected period, which may conveniently be 24 hours. Alternatively, the user's caloric input may be averaged and spread evenly over the user's normal waking hours. The averaged BMR and caloric input data are respectively applied to the minus and plus inputs of summer 36. The sum of the activity, BMR and caloric input data, if positive, as noted previously, represents a net energy increase, and, if negative, represents a net energy decrease. The net energy increase (or decrease) is filtered at 46 so as to reduce relatively short-term variations and transient fluctuations that may be present at the output of summer 36. The filtered net energy input is then converted to a figure representing the corresponding change in the user's body fat percentage at 48, which value may be displayed on display 28. Alternatively, the display 28 may show the net energy increase or decrease directly in calories, which may be compared to a balance and/or to a goal, as described in greater detail below.

The filtered, averaged predicted change in body fat percentage is integrated at 50 over a predetermined extended period such as, for example, one week, since body fat percentage typically changes slowly, and because of possible changes in BMR data during successive measurements. Note that BMR can sometimes change even when a plurality of measurements are taken in quick succession, due to the inherent lack of repeatability in this type of measurement. The result of this integration, which constitutes the predicted change in body fat percentage, is applied to one input of a comparator at 52.

Each time the user of the monitor 10 initiates an update signal to the monitor, the user's current body fat percentage is received, as from the body composition analyzer, at 54. If any body fat percentages were previously received, one or more of these previous measurements may be stored in a memory device, as indicated by Previous % BF (body fat) 56. The previously measured body fat percentage information at 56, which may include the immediately preceding body fat percentage, and/or a running or weighted average of preceding body fat percentages, is then subtracted from the current body fat percentage at summer 58 to compute the actual difference or change in body fat percentage.

The actual change in body fat percentage is calculated by summer 58, and the predicted change in body fat percentage, as calculated by integrator 50, are compared at comparator 52, and the result of that comparison is used to calculate at 60 a correction factor (CF), which is used in subsequent computations of predicted change in body fat percentage and net caloric energy balance. The correction factor is converted into units of calories at 62, and that converted correction factor is averaged at 64 to spread the correction factor calories over, say, a 24-hour period. The averaged correction factor calories are applied to the summer 36 where they are combined with current activity, BMR and input (food) calories to provide either a positive or negative change in the value of net caloric energy. That net value, as noted previously, is filtered at 46 and converted to a new value of predicted change of body fat percentage at 48. This process is repeated each time the user initiates an update such as at the beginning of an exercise or activity period.

Pursuant to one illustrative use of the caloric energy monitor of the invention, relevant information of the user, i.e., his or her height, sex, age, etc., is input to a body composition analyzer. The user stands on the body composition analyzer to provide an estimate of his or her BMR (including digestion), in the manner described in the above-referenced copending patent application. This information is transmitted by the communications link to the monitor 10, which at that time, may be clipped onto the user's belt or wrist a s shown in FIG. 4. However, pursuant to an alternate embodiment, the monitor may be equipped with an input mechanism adapted to accept parameters entered by a user. These parameters may include at least one of BMR, caloric intake, and caloric expenditure.

Monitor 10 then starts to measure activity calories, adding the BMR information input it receives, for example, from the body composition analyzer. If no food is consumed over the relevant period, monitor 10 displays a negative number, which is desirable if the user wants to lose weight. When food is consumed and the approximate number of calories consumed is entered in the monitor 10, this value is added to the previous value of rest and activity calories to provide a caloric energy balance. If too much food is consumed, the value of net caloric energy that is displayed will be positive.

This process is continued, by way of illustration, one week later, when the user updates the monitor with new information obtained from the body composition analyzer. The average caloric energy balance is known for the previous time period, e.g., if there has been a decrease in one pound of fat (one pound of fat=3500 calories) in a seven-day period, then the average balance is –500 calories/day. This average caloric energy balance may optionally be transmitted from the body composition analyzer to the monitor 10 for subsequent display.

Based on the input BMR calories, actual measured activity calories, and calories consumed, the monitor 10 predicts an estimate of energy balance, i.e., –200 calories/day. Since the body fat percentage data received from the body composition analyzer indicated that the actual energy balance was minus 500 calories/day, the monitor 10 computes and enters a correction factor, which in the present example is minus 300 calories, into its energy balance calculation to correct for this error, as described above with reference to FIG. 2. Thus, the subsequent display values of caloric energy balance will be more accurate than the values displayed during the initial or learning period.

This process continues each time the monitor is updated, and the caloric energy balance equation becomes more accurate; that is, the correction factor becomes stable. Even if activity measurement is inaccurate, the energy balance equation has a relatively high accuracy level after several updates with new body fat percentage information. These updates may be obtained from the body composition analyzer device.

Figure 3:
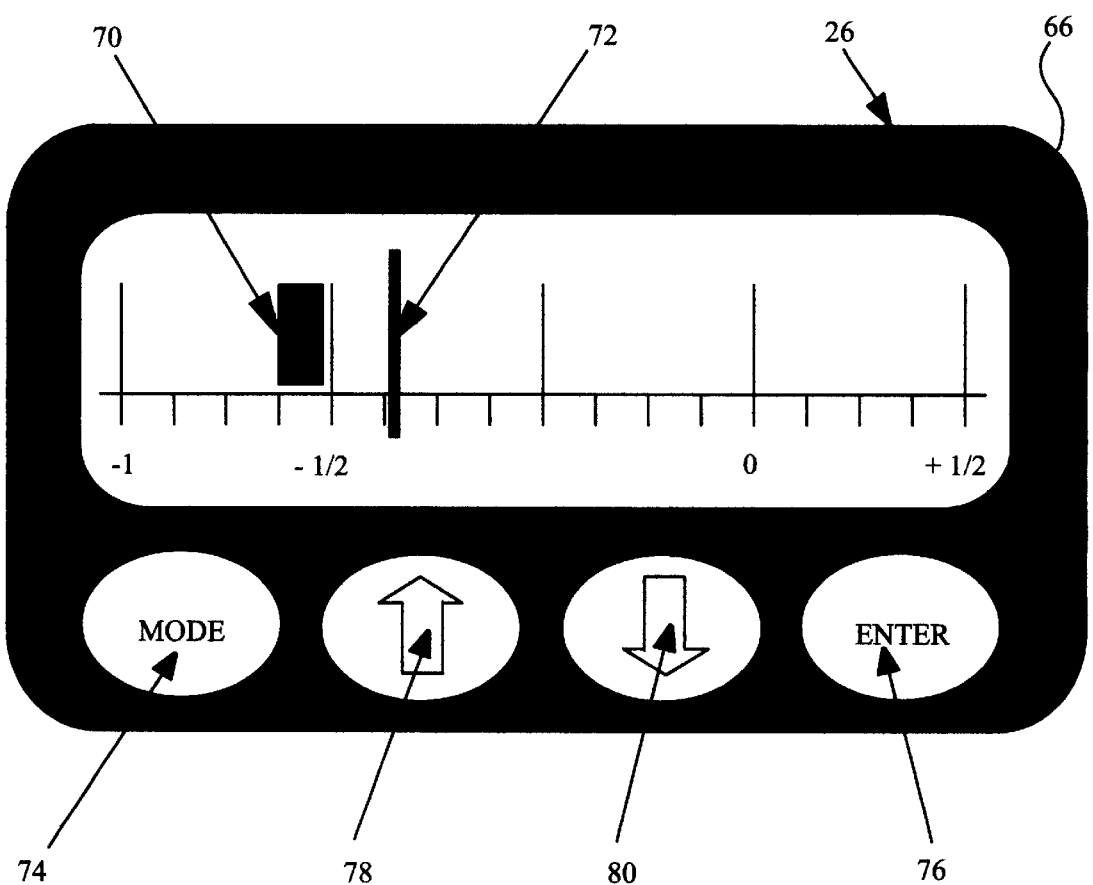
FIG. 3 is an elevational view of a display that can be used with the caloric energy balance monitor of the invention.

As shown in FIG. 3, the display 28 may include a horizontal scale 66 expressed as a percentage change in body fat. The display 28 also may include an indicator 70 of the predicted change in body fat percentage and may also include an indication 72 of goal change in body fat percentage. This "goal change" indication may be established in the body composition analyzer for each user, and is a variable that takes into consideration a given users probability of success. In this manner, the goal change indication provides a mechanism by which users will not be striving to reach impossible goals, and also by which users will be provided with additional challenges if the initial goal is easily reached.

The display 26 may also include a "mode" button, an "enter" button 74, and enter "up" and "down" buttons 78 and 80. An update may be initiated by holding either the mode or enter button down for a certain time, say three seconds. The up and down and enter buttons allow the user to enter his or her calories from food input, either as the total caloric input or as a change from the user's normal food consumption or to correct activity information, and/or to change the user's goal in achieving change in his/her body fat percentage. The up and down buttons also allow the user to override the default goal entry. However, the monitor may be programmed so as to not allow the maximum change in body fat percentage to exceed the amount of total body fat based upon total body displacement (TBD).

It will be appreciated that the caloric energy balance monitor of the invention provides increasingly accurate data of a user's net caloric energy balance. It will also be appreciated that modifications may be made to the embodiment of the invention described hereinabove without departing from the spirit and scope of the invention.

We claim:

1. A caloric energy balance monitor comprising:
   (a) an input mechanism adapted to accept input parameters specifying: base metabolic rate (BMR), physical activity, caloric consumption, and actual changes in body fat or body fat percentage, for an individual;
   (b) a processing mechanism, coupled to the input mechanism, for using the input parameters to calculate an iterative self-improving correction factor by comparing predicted and actual changes in body fat percentage for the individual;
   (c) wherein the processing mechanism uses the correction factor in subsequent computations of predicted changes in body fat percentage so as to improve accuracy of the predicted changes.

2. The caloric energy balance monitor of claim 1 further comprising a display mechanism for indicating current energy balance as calculated by the processing mechanism, wherein the current energy balance is based upon, information entered into the input mechanism; the current energy balance being determined by applying the correction factor to computations of predicted changes in body fat percentage.

3. The caloric energy balance monitor of claim 1 wherein the input parameters correspond to measurements taken across a finite time interval.

4. The caloric energy balance monitor of claim 1 wherein at least one of the input parameters is measured using a body composition analyzer.

5. The caloric energy balance monitor of claim 4 wherein information obtained from the body composition analyzer is the difference between BMR and assumed caloric input.

6. The caloric energy balance monitor of claim 4 wherein information obtained from the body composition analyzer specifies actual pounds or % body fat for the individual.

7. A method for predicting changes in an individual's body fat percentage based upon the individual's caloric balance, the method comprising the steps of:

(a) accepting input parameters specifying: actual change in body fat, base metabolic rate (BMR), physical activity, and caloric consumption for the individual;

(b) using the input parameters to calculate an iterative self-improving correction factor by comparing predicted and actual changes in body fat percentage for the individual;

(c) using the correction factor in subsequent computations of predicted changes in body fat percentage so as to improve accuracy of the predicted changes.

8. The method of claim 7 wherein the input parameters correspond to measurements taken across a finite time interval.

9. A caloric energy balance monitor for monitoring activity, the monitor including:

(d) a mechanism for measuring physical activity;

(e) a processing mechanism for receiving information from a body composition device regarding base metabolic rate, estimated caloric consumption and actual body fat or body fat percentage; and using this information to calculate an iterative self-improving correction factor; and (f) a display.

10. The caloric energy balance monitor of claim 9 wherein the display is equipped to indicate at least one of: current state of energy balance in calories, pounds of body fat, percentage body fat, and weight.

11. The caloric energy balance monitor of claim 9 wherein the processing mechanism calculates the correction factor based on the error between predicted and actual changes in body fat, and incorporates this correction factor into subsequent energy balance calculation to improve the accuracy of these calculations.

* * * * *